United States Patent
Lee et al.

(10) Patent No.: US 8,634,892 B2
(45) Date of Patent: Jan. 21, 2014

(54) DRY ELECTRODE DEVICE AND METHOD OF ASSEMBLY

(71) Applicant: NeuroSky, Inc., San Jose, CA (US)

(72) Inventors: KooHyoung Lee, San Jose, CA (US); ByeongHyeop Choi, Koyang (KR)

(73) Assignee: NeuroSky, Inc., San Jose, CA (US)

( * ) Notice: Subject to any disclaimer, the term of this patent is extended or adjusted under 35 U.S.C. 154(b) by 0 days.

(21) Appl. No.: 13/756,384

(22) Filed: Jan. 31, 2013

(65) Prior Publication Data
US 2013/0211226 A1 Aug. 15, 2013

Related U.S. Application Data

(63) Continuation of application No. 13/433,555, filed on Mar. 29, 2012, now Pat. No. 8,396,529, which is a continuation of application No. 12/116,020, filed on May 6, 2008, now Pat. No. 8,170,637.

(51) Int. Cl.
*A61B 5/04* (2006.01)
*A61B 5/0478* (2006.01)

(52) U.S. Cl.
USPC ............ 600/372; 600/383; 600/394; 607/139

(58) Field of Classification Search
USPC .......... 600/372, 382–386, 394; 607/139, 140, 607/149
See application file for complete search history.

(56) References Cited

U.S. PATENT DOCUMENTS 8,170,637 B2 * 5/2012 Lee et al. ................ 600/372
8,301,218 B2   10/2012 Nguyen et al.
8,396,529 B2 * 3/2013 Lee et al. ................ 600/372

* cited by examiner

*Primary Examiner* — Lee S Cohen
(74) *Attorney, Agent, or Firm* — Van Pelt, Yi & James LLP

(57) ABSTRACT

An electrode set is disclosed that has two separable parts including an assembled base with printed circuit board basement, biasing member and top cover and an electrode. The basement and top cover may be made by metal or conductive material.

20 Claims, 3 Drawing Sheets

DRY ELECTRODE DEVICE AND METHOD OF ASSEMBLY

CROSS REFERENCE TO OTHER APPLICATIONS

This application is a continuation of U.S. patent application Ser. No. 13/433,555, now U.S. Pat. No. 8,396,529, entitled DRY ELECTRODE DEVICE AND METHOD OF ASSEMBLY filed Mar. 29, 2012, which is a continuation of U.S. patent application Ser. No. 12/116,020, now U.S. Pat. No. 8,170,637, entitled DRY ELECTRODE DEVICE AND METHOD OF ASSEMBLY filed May 6, 2008, which are incorporated herein by reference for all purposes.

FIELD

The device relates generally to a dry electrode for skin contact.

BACKGROUND

Electrodes generally are well known and electrodes that can be used to measure an electrical signal of the human body, such as a brain wave. Most of the known electrodes require a special treatment to the head since most currently used electrodes for measuring the brain waves require either electrodes that are wet with gel or needle electrodes. Thus, it is desirable to provide a dry electrode device and it is to this end that the present invention is directed.

DETAILED DESCRIPTION OF ONE OR MORE EMBODIMENTS

The electrode is particularly applicable to the electrode structures described and illustrated below for attached a surface electrode to skin and it is in this context that the electrode set will be described. It will be appreciated, however, that the electrode set has greater utility since it can be assembled or manufactured with different elements than those described below and be within the scope of the electrode set disclosed herein.

Figure 1:
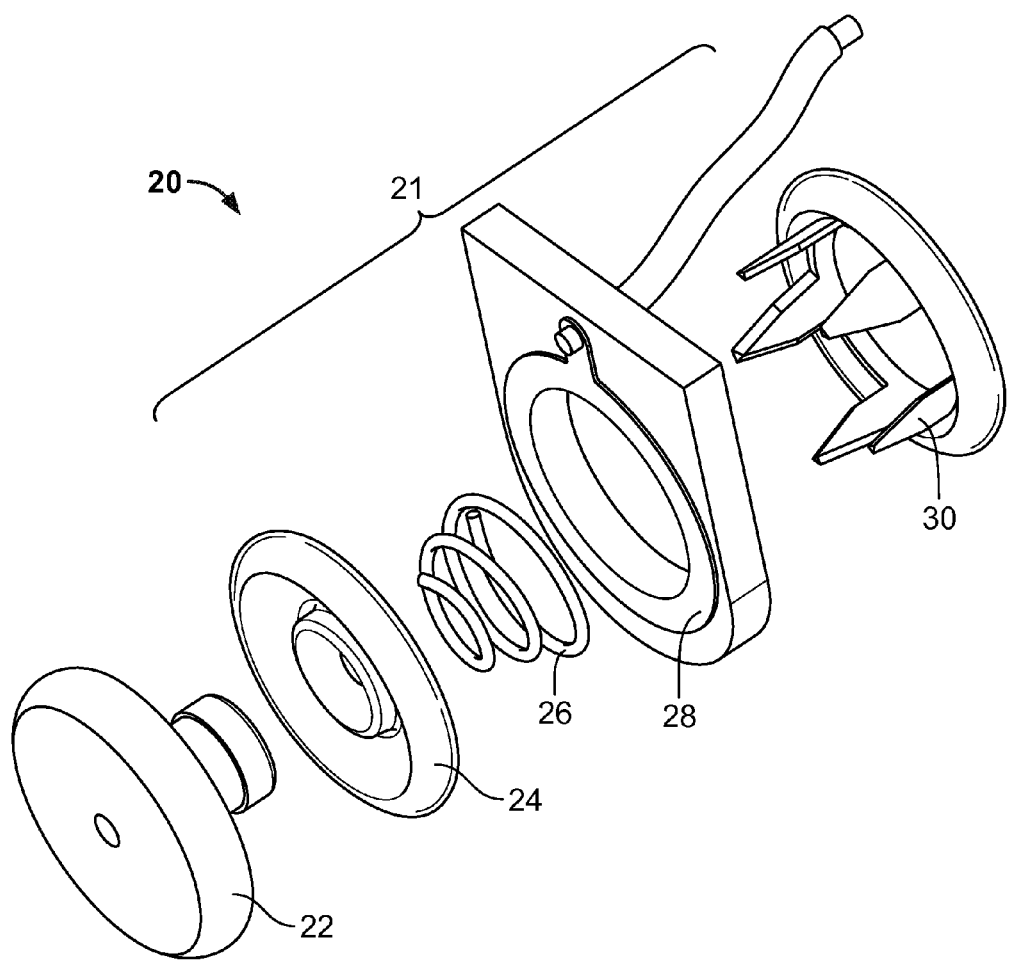
FIGS. 1 and 2 are exploded assembly diagrams of a dry electrode set.
Figure 2:
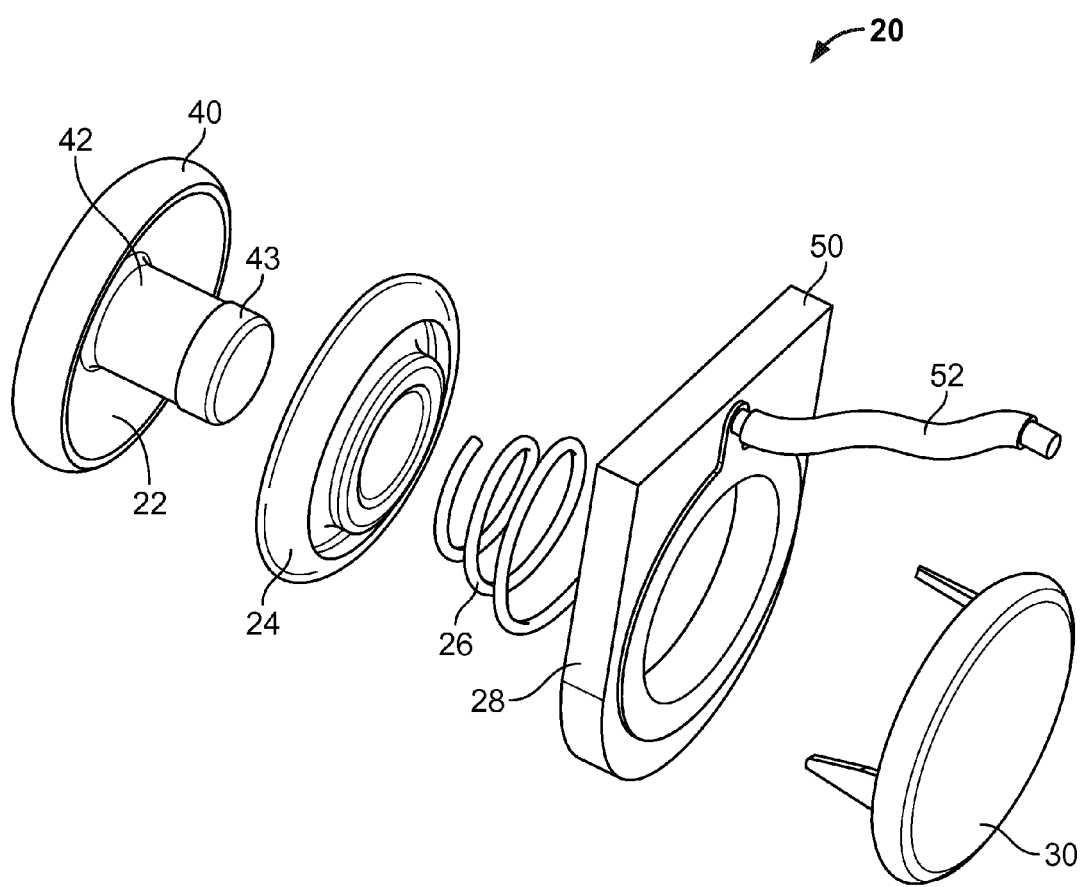

FIGS. 1 and 2 are exploded assembly diagrams of a dry electrode set 20. The electrode set may include two separable parts including a base portion 21 and an electrode 22 wherein the base portion and the electrode can be separated from each other, such as to replace the electrode. The base portion may further comprise a top cover 24, a biasing mechanism 26, such as a spring, a base 28 and a basement 30. The basement 30 with its teeth passes through the base 28, captures the biasing mechanism between the basement and the top cover 24 and secures itself (using the teeth) to the top cover. The basement 30 and the top cover 24 may be made out of a metal or any conductive material.

As shown in FIG. 2, the electrode 22, which is removable and replaceable, may further include an electrode cap portion 40 and an electrode post portion 42 with a retaining ridge 43. The electrode post portion 42 may be press fitted into the top cover 24 so that it engages the biasing mechanism 26 to bias the electrode away from the base 28 so that the retaining ridge 43 is pressed against the top cover. The biasing of the electrode away from the base 28 means that the electrode set, when assembled, can be pressed against the user and the spring will maintain a connection with the skin of the user.

The electrode may be a button type electrode that may be a silver-silver chloride surface electrode or a silver or gold plated surface electrode. The button type electrode may be a dry or wet electrode. In operation, the electrical current being generated based on the measured signal by the electrode passes through the electrode (which is conductive) and the biasing mechanism (which may be metal or conductive) to a connection 52 as described in more detail below. In the electrode set 20, the electrode 22 may have one or more different length electrode post portions 42 so that different pressures may be applied to the skin of the user.

As also shown in FIG. 2, the base 28 may further comprising a set of circuitry 50, such as the circuits on a printed circuit board, and a connection 52, such as a wire, that connects the set of circuitry in the electrode set to a bio-amplifier (not shown) so that a bio-signal which detected by the electrode can be processed. The set of circuitry may include a circuit on the base for connecting the electrode to a bio-amplifier, conductive material and pins for wiring and one or more ASIC chips can be mounted on the base when available.

Figure 3:
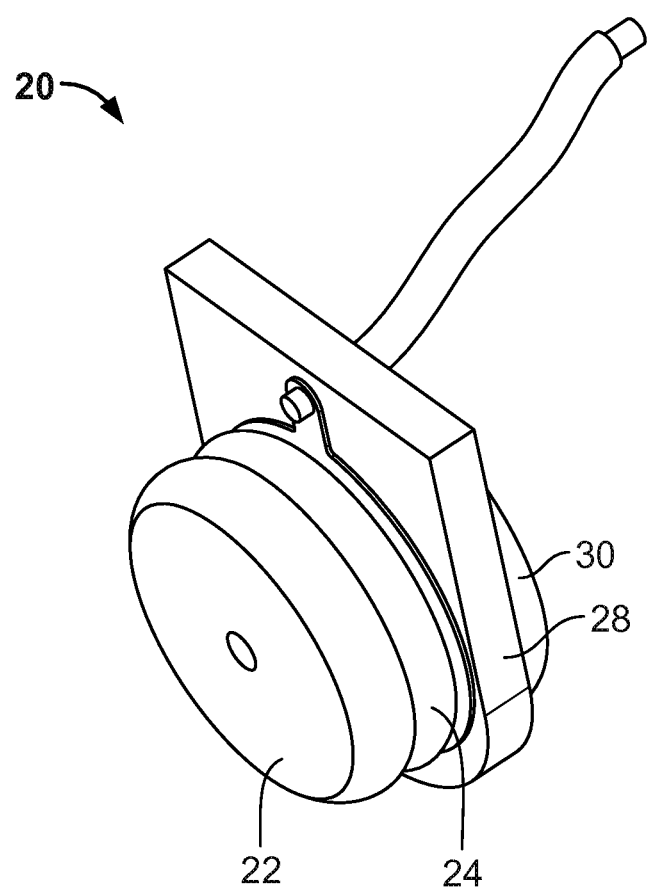
FIG. 3 illustrates an assembled electrode set.

FIG. 3 illustrates an assembled electrode set 20 with the electrode 22, the top cover 24, the base 28 and the basement 30 exposed. When assembled as shown, the electrode 22 is biased away from the base 28 that allows the electrode to pivot in any direction as well as rotate to accommodate the contours of the skin on which the electrode is placed. The biasing of the electrode away from the base 28 also allows the assembled electrode set 20 to be pressed fitted against the skin of the user since the biasing mechanism (not shown in FIG. 3) can compress, but maintain the electrode set in a pressing relationship against the skin of the user.

While the foregoing has been with reference to a particular embodiment of the invention, it will be appreciated by those skilled in the art that changes in this embodiment may be made without departing from the principles and spirit of the invention, the scope of which is defined by the appended claims.

The invention claimed is:

1. A dry electrode set, comprising:
   a base portion, wherein the base portion comprises a base, a conductive biasing mechanism, an opening, and a connection, wherein the base portion further comprises a basement that includes a securing mechanism and a top cover, and wherein the basement with its securing mechanism passes through the base, captures the conductive biasing mechanism between the basement and the top cover and secures itself to the top cover using the securing mechanism;
   a conductive electrode having a cap portion and a post portion connected to the cap portion, the post portion having a retaining mechanism;
   the conductive electrode is inserted into the opening of the base, wherein the conductive electrode is releasably retained in the base by the retaining mechanism, wherein the conductive electrode is pivotable and rotatable in the opening of the base, and wherein the conductive electrode is biased away from the base and allows for the conductive electrode to be pressed fitted against a user's skin; and
   wherein a signal detected by the conductive electrode passes through the conductive electrode and the conductive biasing mechanism to the connection.

2. The dry electrode set of claim 1, wherein the securing mechanism includes teeth, and wherein the basement with its teeth passes through the base, captures the conductive biasing mechanism between the basement and the top cover and secures itself to the top cover using the teeth.

3. The dry electrode set of claim 1, wherein the conductive electrode is replaceable.

4. The dry electrode set of claim 1, wherein the base is located between the conductive electrode and the basement.

5. The dry electrode set of claim 1, wherein the retaining mechanism includes a retaining ridge.

6. The dry electrode set of claim 1, wherein the conductive biasing mechanism further comprises a spring.

7. The dry electrode set of claim 1, wherein the base further comprises a set of circuits and the top cover connected to each other.

8. The dry electrode set of claim 1, wherein the conductive biasing mechanism further comprises a spring, and wherein the base further comprises a set of circuits and the top cover connected to each other.

9. The dry electrode set of claim 1, wherein the conductive electrode comprises a silver-silver chloride surface electrode.

10. The dry electrode set of claim 1, wherein a surface of the conductive electrode includes gold or silver.

11. The dry electrode set of claim 1, wherein the conductive electrode comprises a button type electrode.

12. A dry electrode set, comprising:
a base portion, wherein the base portion comprises a base, a conductive biasing mechanism, an opening, and a connection, wherein the base portion further comprises a basement that includes teeth and a top cover, wherein the basement with its teeth passes through the base, captures the conductive biasing mechanism between the basement and the top cover and secures itself to the top cover using the teeth, and wherein the conductive biasing mechanism further comprises a spring;
a conductive electrode having a cap portion and a post portion connected to the cap portion, the post portion having a retaining mechanism;
the conductive electrode is inserted into the opening of the base, wherein the conductive electrode is releasably retained in the base by the retaining mechanism, wherein the conductive electrode is pivotable and rotatable in the opening of the base, wherein the conductive electrode is biased away from the base and allows for the conductive electrode to be pressed fitted against a user's skin; and
wherein a signal detected by the conductive electrode passes through the conductive electrode and the conductive biasing mechanism to the connection.

13. The dry electrode set of claim 12, wherein the top cover is located between the conductive electrode and the basement.

14. The dry electrode set of claim 12, wherein the conductive electrode is replaceable.

15. The dry electrode set of claim 12, wherein the base further comprises a set of circuits and the top cover connected to each other.

16. The dry electrode set of claim 12, wherein the conductive electrode is replaceable, and wherein the base further comprises a set of circuits and the top cover connected to each other.

17. The dry electrode set of claim 12, wherein the conductive electrode comprises a silver-silver chloride surface electrode.

18. The dry electrode set of claim 12, wherein a surface of the conductive electrode includes gold or silver.

19. The dry electrode set of claim 12, wherein the conductive electrode comprises a button type electrode.

20. A dry electrode set, comprising:
a base portion, wherein the base portion comprises a base, a conductive biasing mechanism, an opening, and a connection, wherein the base portion further comprises a basement that includes teeth and a top cover, wherein the basement with its teeth passes through the base, captures the conductive biasing mechanism between the basement and the top cover and secures itself to the top cover using the teeth, wherein the base further comprises a set of circuits and the top cover connected to each other, wherein the conductive biasing mechanism further comprises a spring;
a conductive electrode having a cap portion and a post portion connected to the cap portion, the post portion having a retaining ridge, wherein the conductive electrode is replaceable, and wherein the conductive electrode comprises a button type electrode;
the conductive electrode is inserted into the opening of the base, wherein the conductive electrode is releasably retained in the base by the retaining ridge, wherein the conductive electrode is pivotable and rotatable in the opening of the base, wherein the conductive electrode is biased away from the base and allows for the conductive electrode to be pressed fitted against a user's skin;
wherein a signal detected by the conductive electrode passes through the conductive electrode and the conductive biasing mechanism to the connection; and
wherein the top cover is located between the conductive electrode and the base.

\* \* \* \* \*